(12) United States Patent
Miyazaki et al.

(10) Patent No.: US 7,914,596 B2
(45) Date of Patent: Mar. 29, 2011

(54) AIR PURIFIER

(75) Inventors: Haruhito Miyazaki, Nara (JP); Takeshi Furukawa, Kashiba (JP); Shinichiroh Murayama, Kobe (JP); Ryuhji Asakura, Tondabayashi (JP)

(73) Assignee: Sharp Kabushiki Kaisha, Osaka-Shi (JP)

( * ) Notice: Subject to any disclaimer, the term of this patent is extended or adjusted under 35 U.S.C. 154(b) by 504 days.

(21) Appl. No.: 11/909,261

(22) PCT Filed: Mar. 15, 2006

(86) PCT No.: PCT/JP2006/305101
§ 371 (c)(1),
(2), (4) Date: Sep. 20, 2007

(87) PCT Pub. No.: WO2006/100976
PCT Pub. Date: Sep. 28, 2006

(65) Prior Publication Data
US 2009/0056289 A1 Mar. 5, 2009

(30) Foreign Application Priority Data

Mar. 22, 2005 (JP) ................... 2005-081114
Mar. 22, 2005 (JP) ................... 2005-081118
Mar. 22, 2005 (JP) ................... 2005-081119

(51) Int. Cl.
*B01D 50/00* (2006.01)
*B01D 59/50* (2006.01)

(52) U.S. Cl. ................. 55/332; 55/418; 55/429; 55/471

(58) Field of Classification Search .................... 55/315, 55/320, 332, 394, 395, 367, 418, 467, 471, 55/472, 429, 434; 96/380, 384, 385
See application file for complete search history.

(56) References Cited

U.S. PATENT DOCUMENTS

| | | | | | |
|---|---|---|---|---|---|
| 2,323,405 | A | * | 7/1943 | Linderoth, Jr. | 55/395 |
| 2,384,414 | A | * | 9/1945 | Antrim | 55/329 |
| 2,491,645 | A | * | 12/1949 | Clark et al. | 96/336 |
| 3,364,664 | A | * | 1/1968 | Doane | 55/394 |
| 3,385,032 | A | * | 5/1968 | Crabbe | 96/324 |
| 3,543,325 | A | * | 12/1970 | Hamrick | 15/314 |
| 3,936,284 | A | * | 2/1976 | Mason | 96/117.5 |

(Continued)

FOREIGN PATENT DOCUMENTS

JP 55-25112 U 2/1980

(Continued)

*Primary Examiner* — Duane Smith
*Assistant Examiner* — Sonji Turner
(74) *Attorney, Agent, or Firm* — Birch, Stewart, Kolasch & Birch, LLP

(57) ABSTRACT

Behind a front panel of an air purifier are formed guide paths on the right and left sides thereof. A space between the front panel and a filter unit is partitioned by a partition plate into a front panel rear space and a filter unit front space. Part of an airflow that has entered the guide path through an air intake enters the filter unit front space, and the other part thereof enters the front panel rear space. When entering the front panel rear space, the airflow takes a sharp turn at a sharp turn corner. As a result, coarse dust is separated from the airflow, and the separated coarse dust falls into a dust box.

20 Claims, 14 Drawing Sheets

U.S. PATENT DOCUMENTS

| | | | | |
|---|---|---|---|---|
| 4,172,865 A | * | 10/1979 | Steier | 261/62 |
| 5,097,750 A | * | 3/1992 | Oldham et al. | 454/63 |
| 5,281,246 A | * | 1/1994 | Ray et al. | 55/302 |
| D360,028 S | * | 7/1995 | Matsuda | D23/364 |
| 6,053,968 A | * | 4/2000 | Miller | 96/224 |
| D489,800 S | * | 5/2004 | Tokunaga | D23/364 |
| D503,972 S | * | 4/2005 | Pippel et al. | D23/355 |
| D521,135 S | * | 5/2006 | Kita | D23/364 |
| 7,537,649 B2 | * | 5/2009 | Pippel et al. | 96/417 |

FOREIGN PATENT DOCUMENTS

| | | |
|---|---|---|
| JP | 52-79829 A | 4/1987 |
| JP | 54-11519 A | 1/1989 |
| JP | 54-28427 A | 1/1989 |
| JP | 4-70121 U | 6/1992 |
| JP | 2002-113316 A | 4/2002 |
| JP | 2002-349918 A | 12/2002 |
| JP | 3460818 B2 | 10/2003 |
| JP | 2004-50084 A | 2/2004 |

* cited by examiner

AIR PURIFIER

BACKGROUND OF THE INVENTION

1. Field of the Invention

The present invention relates to air purifiers that remove contaminants, such as dust and cigarette smoke, from indoor air.

2. Description of the Related Art

In present-day life, particulates that are hazardous to health, such as pollen and dust, enter the house through different openings. For this reason, the need for air purifiers is increasing year by year.

Air purifiers capture airborne dust and contaminants by circulating the indoor air. Particles of different sizes are suspended in the air, and they are usually captured in stages in decreasing order of size. Among them, coarse dust such as lint is conventionally captured with a netted "pre-filter". In recent years, however, several proposals have been made to capture coarse dust with a cyclone device. An example of an air purifier provided with a cyclone device is seen in Patent Document 1.

Patent Document 1: JP-A-2002-349918 (pages 3 and 4, FIGS. 1 to 3)

SUMMARY OF THE INVENTION

Problems to be Solved by the Invention

To achieve a cyclone device with a superior dust capturing capability, it is necessary to suck in high volumes of air and whirl the air around at high speed. This inevitably increases the level of noise. Such a high level of noise may be allowed for such an item as a vacuum cleaner that is used for a limited period of time, but is fatal to such an item as an air purifier that is continuously operated for a long period of time. In view of the conventionally experienced problem described above, it is an object of the present invention to provide air purifiers that can capture coarse dust in the air without using a filter, and that are less noisy than cyclone devices.

Means for Solving the Problem

To achieve the above object, according to one aspect of the present invention, in an air purifier provided with: an air blower circulating indoor air; a filter unit placed in a circulating airflow of the indoor air, the filter unit capturing dust in the air; and a guide path guiding the indoor air to the filter unit, the guide path is followed by a sharp turn corner for the airflow, and a coarse dust collector collecting coarse dust separated from the airflow that has made a sharp turn.

With this structure, the separation mechanism for separating the coarse dust by making the airflow take a sharp turn helps achieve sufficient separation capability to capture the coarse dust in the air. Unlike a cyclone device, since the air is not continuously whirled around, it achieves a lower noise level. This makes it suitable for an air purifier that is used continuously in the room.

Preferably, according to the invention, in the air purifier structured as described above, the guide path is formed behind a front panel placed in front of the filter unit, the front panel has rear-facing air intakes formed on the right and left sides thereof, and the sharp turn corner just past the entry of each air intake, and in a lower portion of the front panel is provided a detachable dust box serving as the coarse dust collector.

With this structure, the coarse dust is captured behind the front panel that is commonly provided in the air purifier. This makes it possible to achieve an air purifier that is mechanically reasonable and comfortable in terms of design. In addition, since the coarse dust is collected in the detachable dust box, it is possible to dispose of it without dirtying one's hands.

Preferably, according to the invention, in the air purifier structured as described above, a space between the front panel and the filter unit is partitioned by a vertical partition plate into a front panel rear space and a filter unit front space. The partition plate faces, at the right and left ends thereof, the sharp turn corners, and a space between the front panel and the partition plate becomes narrower at the right and left ends thereof and becomes broader in the middle thereof. In an upper portion of the partition plate are formed a plurality of air vents arranged in a horizontal row, so that the front panel rear space is communicated with the filter unit front space.

With this structure, the airflow that has turned at the sharp turn corner and then entered the front panel rear space slows down as it approaches the middle of the partition plate because the space is widened at that point. This enables efficient separation of the coarse dust. Since the airflow passes through the air vents into the filter unit front space, leaving the coarse dust behind, the coarse dust falls into the coarse dust collector. Due to the partition plate provided between the falling coarse dust and the filter unit, the coarse dust falls into the dust box without sticking to the filter unit. This makes it possible to collect the coarse dust in the dust box without fail.

Preferably, according to the invention, a space between the front panel and the filter unit is partitioned by a vertical partition plate into a front panel rear space and a filter unit front space. The partition plate faces, at the right and left ends thereof, the sharp turn corners, and a space between the front panel and the partition plate becomes narrower at the right and left ends thereof and becomes broader in the middle thereof. At the right and left ends of the partition plate are provided diverting guide paths diverting the air that has entered the front panel rear space into the filter unit front space. The diverting guide paths each have a second sharp turn corner and a second coarse dust collector.

With this structure, the airflow that has turned at the sharp turn corner and then entered the front panel rear space slows down as it approaches the middle of the partition plate because the space is widened at that point. This enables efficient separation of the coarse dust. Since the airflow passes through the air vents into the filter unit front space, leaving the coarse dust behind, the coarse dust falls into the coarse dust collector. Due to the partition plate provided between the falling coarse dust and the filter unit, the coarse dust falls into the dust box without sticking to the filter unit. This makes it possible to collect the coarse dust in the dust box without fail. Additionally, the coarse dust is captured once again with the second sharp turn corner and the second coarse dust collector when the air inside the front panel rear space is guided to the filter unit front space. This makes it possible to feed the air containing a smaller amount of coarse dust to the filter unit, thereby preventing clogging of the filter unit.

Preferably, according to the invention, in the air purifier structured as described above, a netted filter is provided at the entry of the filter unit front space facing the guide path.

With this structure, the air that directly enters the filter unit front space from the guide path is made to pass through the netted filter. As a result, even if coarse dust is still carried by the air, it is captured by the netted filter before reaching the filter unit.

Preferably, according to the invention, in the air purifier structured as described above, a netted filter is provided in an air passage between the front panel rear space and the filter unit front space.

With this structure, the air moving from the front panel rear space to the filter unit front space is made to pass through the netted filter. As a result, even if coarse dust is still carried by the air, it is captured by the netted filter before reaching the filter unit.

Preferably, according to the invention, in the air purifier structured as described above, the guide path is formed in a lower portion of a front panel placed in front of the filter unit. At the back of the guide path is formed the sharp turn corner that makes the airflow take a sharp upward turn and thereby guides the airflow to a front of the filter unit. The front panel is fitted with a dust box in a position located above the guide path, the dust box collecting the coarse dust separated from the airflow sucked into the filter unit.

With this structure, the airflow that has taken a sharp upward turn is gradually sucked into the filter unit while moving linearly upward along the filter unit. The airflow takes a right-angled turn when it is sucked into the filter unit. On the other hand, the coarse dust in the airflow keeps moving inertially. Upon reaching the upper portion of the airflow passage, the coarse dust is separated, by the swirling flow formed between the front panel and the filter unit, from the airflow that is being sucked into the filter unit, and then falls into the dust box by gravity. This makes it possible to collect the coarse dust in the airflow in the dust box without making it stick to the filter unit. Unlike a cyclone device, since the air is not continuously whirled around, it achieves a lower noise level. This makes it suitable for an air purifier that is used continuously in the room.

Preferably, according to the invention, in the air purifier structured as described above, the guide path is built with upper and lower air guide plates that guide the indoor air obliquely downward.

With this structure, the airflow moves obliquely downward, takes a turn at a sharp angle, and then moves upward. This increases the speed at which the airflow moves and hence the inertial force of the coarse dust. As a result, coarse dust separation capability is improved.

Preferably, according to the invention, in the air purifier structured as described above, the lower air guide plate is curved downward, as seen in a front view.

With this structure, the pressures between an area of the guide path closer to the air blower and an area thereof farther away from the air blower are equalized. This makes the airflow move straight, as seen in a front view, resulting in an increase in the speed at which the airflow moves. As a result, it is possible to improve coarse dust separation capability.

Preferably, according to the invention, in the air purifier structured as described above, the cross-sectional area of the guide path is approximately the same as the cross-sectional area of an airflow passage on the most upstream side of the filter unit.

With this structure, the airflow from the guide path passes straight through the airflow passage on the most upstream side of the filter unit, resulting in an increase in the speed at which the airflow moves. This makes it possible to improve coarse dust separation capability.

Preferably, according to the invention, in the air purifier structured as described above, in a space between the filter unit and a front panel placed in front of the filter unit, an air guide plate is disposed diagonally to the filter unit in a horizontal plane, such that the guide path is formed between the air guide plate and the filter unit. The guide path has a larger-width end at one end of the air guide plate, and has a smaller-width end at the other end thereof. The guide path is provided, at the larger-width end thereof, with an air intake leading to the outside, and provided, at the smaller-width end thereof, with the sharp turn corner communicating with the coarse dust collector located between the air guide plate and the front panel.

With this structure, the airflow that has entered the guide path through the air intake is gradually sucked into the filter unit while moving horizontally along the guide path. The airflow takes a right-angled turn when it is sucked into the filter unit. On the other hand, the coarse dust in the airflow keeps moving straight inertially. Upon reaching the innermost portion of the guide path, the airflow turns the sharp turn corner into the coarse dust collector. This sharp turn of the airflow causes the coarse dust to be separated from the airflow. The separated coarse dust falls by gravity and collects at the bottom of the coarse dust collector. This makes it possible to collect the coarse dust in the airflow in the coarse dust collector without making it stick to the filter unit. Unlike a cyclone device, since the air is not continuously whirled around, it achieves a lower noise level. This makes it suitable for an air purifier that is used continuously in the room.

Preferably, according to the invention, in the air purifier structured as described above, the air guide plate has formed therein an air vent for circulating the air that has flowed into the coarse dust collector back into the guide path.

With this structure, the air flows smoothly from the guide path to the coarse dust collector, making it possible to efficiently introduce the coarse dust into the coarse dust collector.

Preferably, according to the invention, in the air purifier structured as described above, the air vent is formed in an upper portion of the coarse dust collector.

With this structure, the airflow is made to pass through an area away from the coarse dust collected in the bottom of the coarse dust collector. This prevents the collected coarse dust from being stirred up and drawn back into the airflow.

Preferably, according to the invention, in the air purifier structured as described above, the air vent is disposed near the air intake.

With this structure, the air inside the coarse dust collector is sucked in to the entry of the guide path. As a result, even when the air still contains dust, the dust is captured by the filter unit, or is separated from the airflow when the airflow takes another turn at the sharp turn corner. This helps realize a thorough removal of dust.

Preferably, according to the invention, in the air purifier structured as described above, in a lower portion of the coarse dust collector, a detachable dust box is provided.

With this structure, it is possible to take out the dust box and dispose of the coarse dust collected therein without dirtying one's hands.

Preferably, according to the invention, in the air purifier structured as described above, two of the air guide plates are provided so as to be symmetric, and a divider plate is provided between the air guide plates to form the sharp turn corners on the right and left sides thereof.

With this structure, irrespective of whether the airflow is sucked in from the right or left side, the airflow is guided from the ends of the filter unit to the middle thereof, that is, from a region where the suction power of the air blower is relatively weak to a region where the suction power is relatively strong. This results in the formation of a stable airflow that can reach the innermost portion of the guide path without fail.

Preferably, according to the invention, in the air purifier structured as described above, the dust box singly covers both right and left sections of the coarse dust collector.

With this structure, the number of dust boxes is smaller than that of coarse dust collectors. This reduces the trouble of disposing of the coarse dust.

Preferably, according to the invention, in the air purifier structured as described above, the coarse dust collector has a multiple-tiered structure.

With this structure, the distance over which the coarse dust in each coarse dust collector falls is decreased, allowing the coarse dust to quickly reach the bottom of the coarse dust collector. This makes it possible to reduce the percentage of coarse dust that will be carried away by the airflow before it reaches the bottom.

ADVANTAGES OF THE INVENTION

According to the present invention, a sucked air is made to take a sharp turn at a sharp turn corner for the separation of coarse dust before it reaches a filter unit. This makes it possible to capture the coarse dust in the air at a necessary and sufficient level without using a filter. Additionally, this coarse dust separation mechanism achieves a lower noise level than that of a cyclone device, causing no harm to the commercial value of an air purifier.

DETAILED DESCRIPTION OF THE INVENTION

Figure 1:
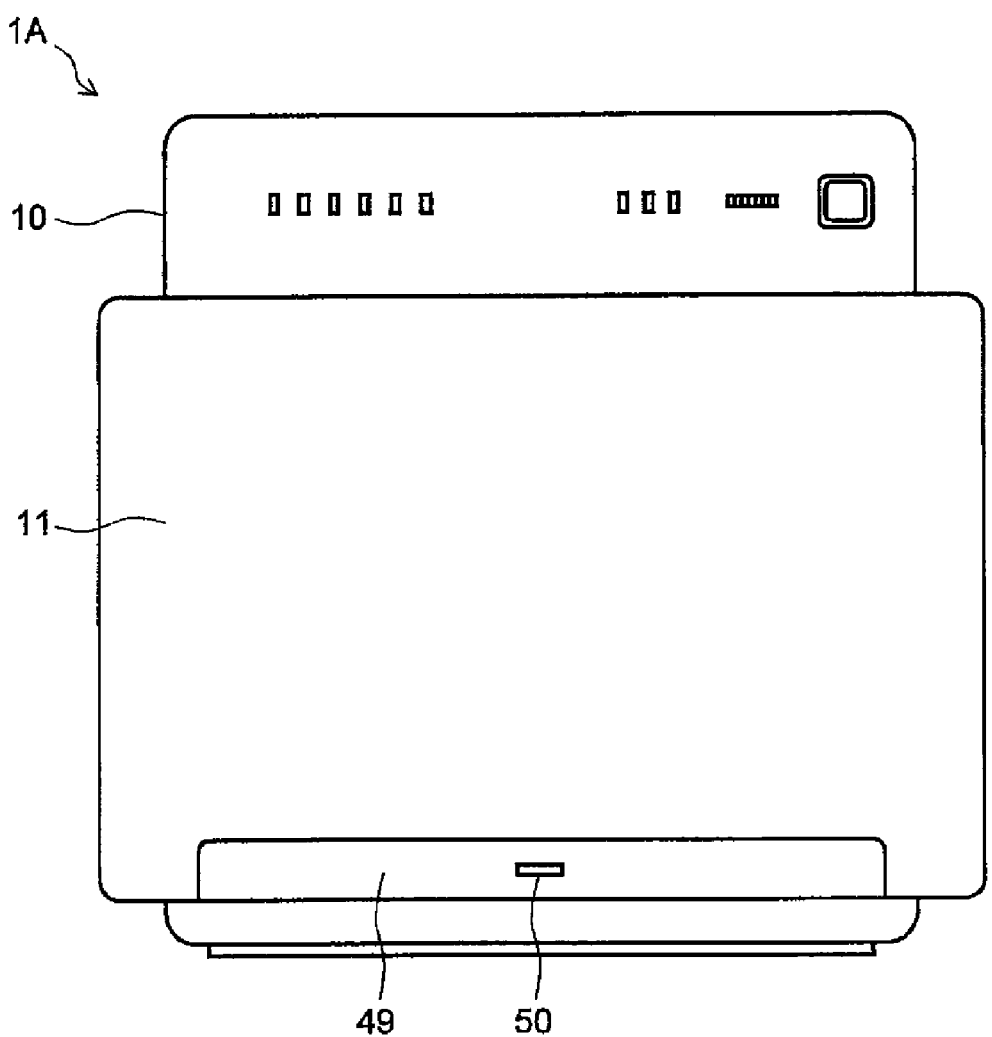
FIG. 1 is a front view of an air purifier according to a first embodiment of the invention.
Figure 2:
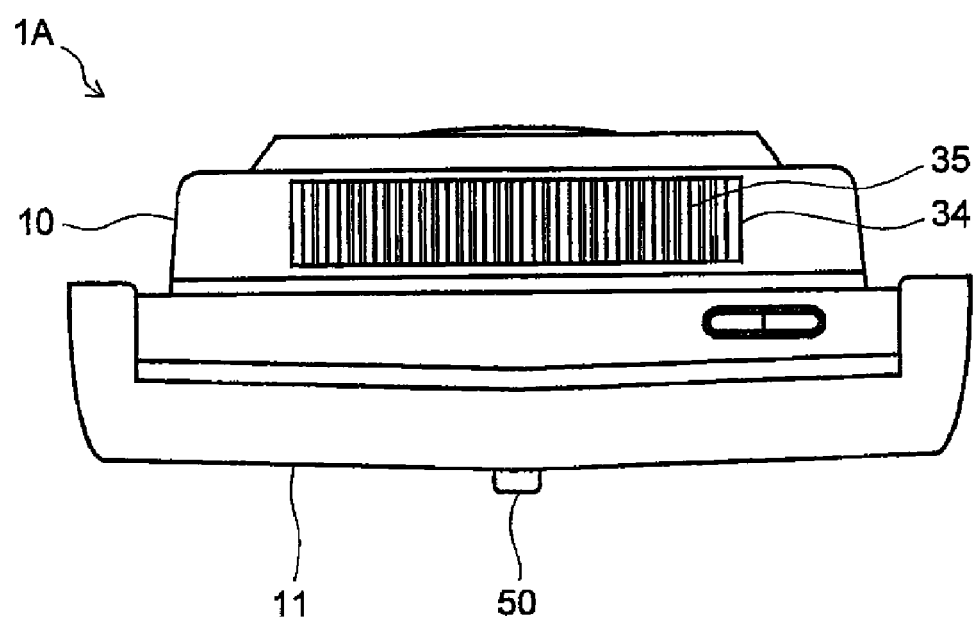
FIG. 2 is a top view of the air purifier of the first embodiment.
Figure 3:
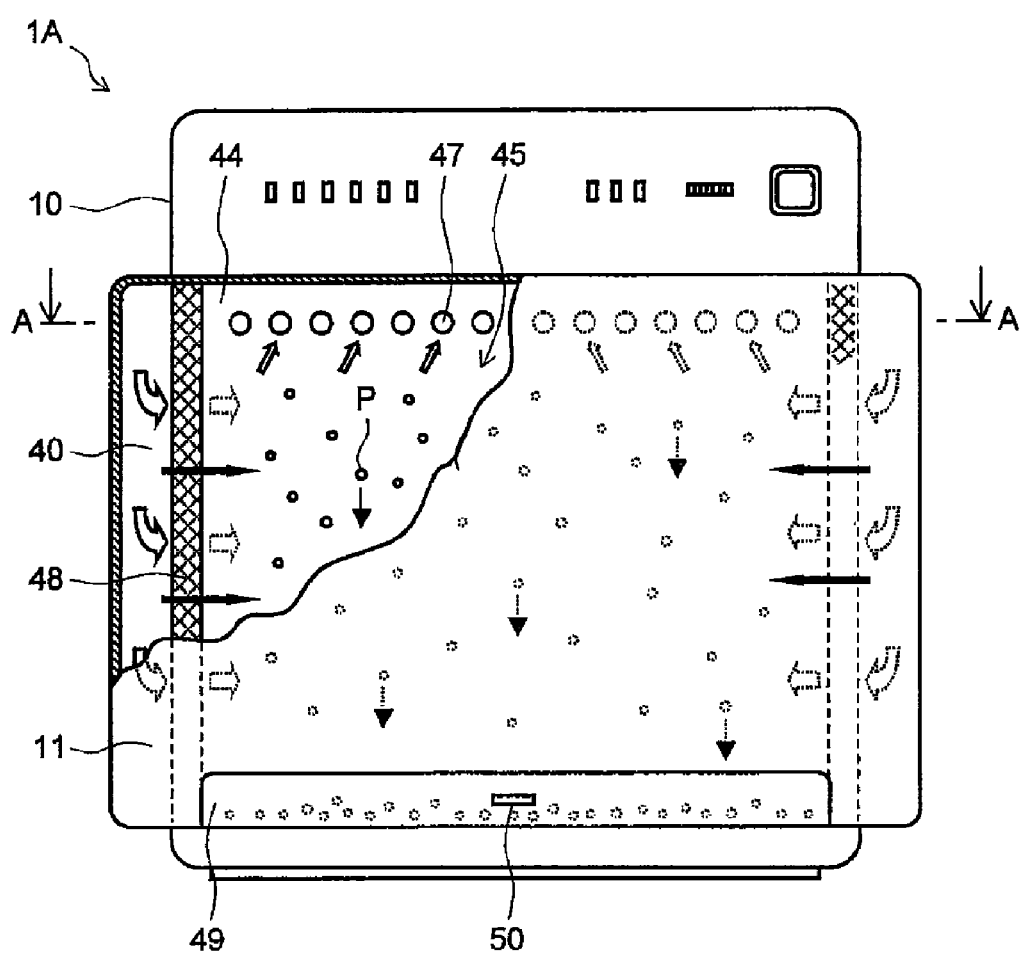
FIG. 3 is a partial cutaway front view of the air purifier of the first embodiment.
Figure 4:
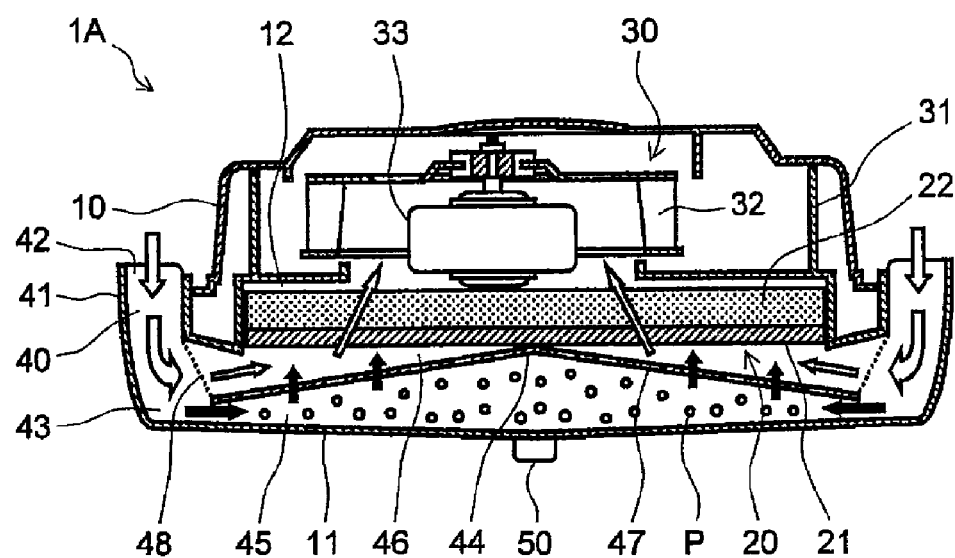
FIG. 4 is a sectional view taken on the line A-A of FIG. 3.

Hereinafter, a first embodiment of the present invention will be described with reference to FIGS. 1 to 4. FIG. 1 is a front view of an air purifier, FIG. 2 is a top view of the air purifier, FIG. 3 is a partial cutaway front view of the air purifier, and FIG. 4 is a sectional view taken on the line A-A of FIG. 3.

An enclosure of an air purifier 1A according to the first embodiment is mainly composed of a main body 10 in the shape of an upright flat box and a front panel 11 fitted detachably to the front face of the main body 10. On the front face of the main body 10, a filter unit housing recess 12 is formed (see FIG. 4), where a filter unit 20 formed with a dust collecting filter 21 and an odor removal filter 22 situated at the rear of the dust collecting filter 21 is housed. The dust collecting filter 21 captures fine dust in the air; the odor removal filter 22 removes odors in the air with the help of activated charcoal or the like. The filter unit 20 is supported in such a way that a dust capturing face thereof is held in a vertical position.

Behind the filter unit housing recess 12 is provided an air blower 30 that sucks in air through the filter unit 20. The air blower 30 is composed of a fan casing 31 formed inside the main body 10, a sirocco fan 32 provided inside the fan casing 31, and a motor 33 for rotating the sirocco fan 32. In the upper surface of the main body 10 is formed an air outlet 34 for the fan casing 31 (see FIG. 2). The air outlet 34 is provided with a grille 35.

Behind the front panel 11, guide paths 40 for guiding the indoor air to the filter unit 20 are formed as follows. That is, at the right and left ends of the front panel 11, there are formed integrally air guide plates 41, each being bent backward at almost a right angle and bowed outward (see FIG. 4). The air guide plates 41 each face the side face of the main body 10 with a space left between them. This space serves as the guide path 40. Provided at the entries of the guide paths 40 are rear-facing air intakes 42. The guide paths 40 extend forward from the air intakes 42, and reach sharp turn corners 43 where the front panel 11 and the air guide plates 41 are joined together. The airflow moving along the guide paths 40 takes a sharp, almost right-angled turn at the sharp turn corners 43.

The space between the front panel 11 and the filter unit 20 is partitioned by a vertical partition plate 44 into two spaces. Of these two spaces, one is a front panel rear space 45 located between the partition plate 44 and the front panel 11, and the other is a filter unit front space 46 located between the partition plate 44 and the filter unit 20. As shown in FIG. 4, the partition plate 44 faces, at the right and left ends thereof, the sharp turn corners 43, and is bent in the middle thereof to form an inverted V shape. This makes the space between the partition plate 44 and the front panel 11 narrower at the right and left ends of the partition plate 44, and makes it broader in the middle thereof.

In the upper portion of the partition plate 44 are formed a plurality of air vents 47 arranged in a horizontal row, so that the front panel rear space 45 is communicated with the filter unit front space 46. Netted filters 48 are provided at the entries of the filter unit front space 46 facing the guide paths 40.

At the base of the front panel rear space 45 is provided a detachable dust box 49 that serves as a coarse dust collector for collecting coarse dust separated from the airflow. The dust box 49, which has almost the same front width as that of the partition plate 44, is formed as a drawer, so that the user can pull it out with a knob 50. The shape of the dust box 49 is almost the same as that of the front panel rear space 45. That is, the dust box 49 is bulging at the middle thereof toward the filter unit 20. This helps increase the capacity of the dust box 49.

The air purifier 1A operates as follows. When the air blower 30 is driven, a negative pressure is produced behind the filter unit 20. This results in the formation of the airflow that is sucked in through the air intakes 42, passes through the filter unit 20, and is then blown out of the air outlet 34. Part of the airflow sucked in through the air intakes 42 passes through the filters 48 and enters the filter unit front space 46. Since the airflow flowing through the guide path 40 takes a sharp turn to enter the filter unit front space 46, much of the coarse dust P in the airflow moves straight forward inertially. Any coarse dust P trying to enter the filter unit front space 46 is blocked by the filter 48.

The other part of the airflow, which has not entered the filter unit front space 46, takes a sharp turn at the sharp turn corners 43 and then enters the front panel rear space 45. The coarse dust P in the airflow also enters the front panel rear space 45 along with the airflow. As mentioned above, since the air guide plates 41 are bowed outward, the airflow is led toward the front panel rear space 45 as it moves along the inner surfaces of the air guide plates 41, and becomes a laminar flow before it reaches the sharp turn corners 43. This laminar flow turns smoothly at the sharp turn corners 43, making effective separation of the coarse dust possible.

The airflow that has entered the front panel rear space 45 slows down as it approaches the middle of the partition plate 44 because the front panel rear space 45 is widened at that point. As a result, the coarse dust P is separated from the airflow, and then falls into the dust box 49. The airflow from which the coarse dust P is separated passes through the air vents 47 into the filter unit front space 46. The air vents 47 are formed only in the upper portion of the partition plate 44, and no air vents 47 are formed in the lower portion of the partition plate 44. This prevents falling coarse dust P from being drawn to the filter unit 20, ensuring that the coarse dust P falls into the dust box 49.

The air that has entered the filter unit front space 46 passes through the filter unit 20, and is then sucked in by the air blower 30. In that process, fine dust in the air is captured by the dust collecting filter 21, and odors are removed by the odor removal filter 22. The space between the partition plate 44 and the filter unit 20 is the largest at both ends of the partition plate 44, and is increasingly smaller toward the middle thereof. This configuration gives the partition plate 44 a role as a pressure equalizing plate for equalizing a suction pressure that acts on the filter unit 20.

The air that has purified by the filter unit 20 is blown out of the air outlet 34. In this way, the circulation of the airflow is produced in a room such that the air is sucked in horizontally through the air intakes 42 and is then blown out of the air outlet 34 in the upward direction.

As the air purifier 1A is continuously operated, the coarse dust P is gradually collected in the dust box 49. When the amount of collected coarse dust becomes large, the air purifier 1A is stopped, and the dust box 49 is taken out for the disposal of the coarse dust P collected therein. The emptied dust box 49 is reinstalled in the air purifier 1A, and the operation is resumed. Preferably, at least part of the dust box 49 is made of transparent material, so that the amount of coarse dust collected therein can be seen though at a glance.

The separation mechanism for separating the coarse dust P by making the airflow take a sharp turn gives the air purifier 1A sufficient separation capability to capture the coarse dust P in the air. Unlike a cyclone device, since the air is not continuously whirled around, it achieves a lower noise level. This makes it suitable for an air purifier that is used continuously in the room. In addition, the coarse dust P is captured behind the front panel 11. Since the front panel 11 is a commonly used member of the air purifier, it is mechanistically reasonable and comfortable in terms of design.

Figure 5:
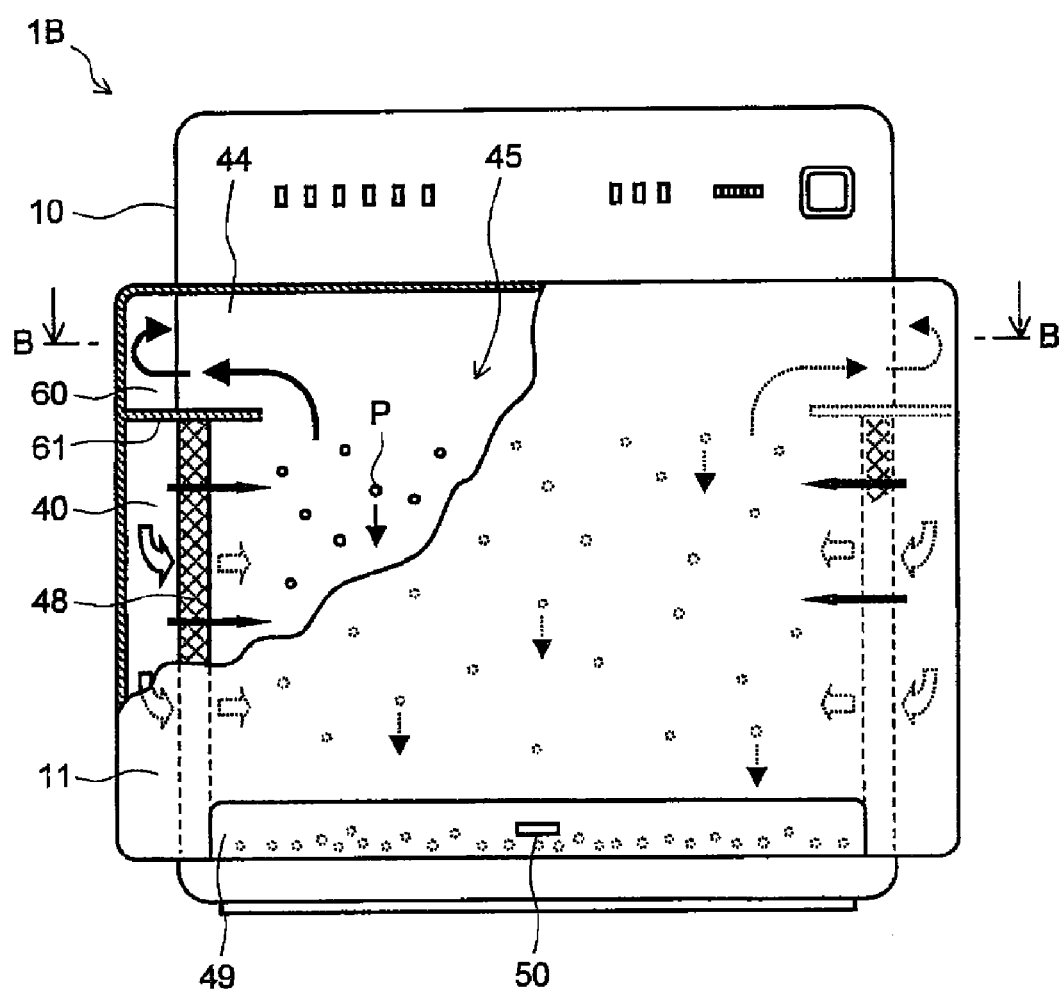
FIG. 5 is a partial cutaway front view of an air purifier according to a second embodiment of the invention.
Figure 6:
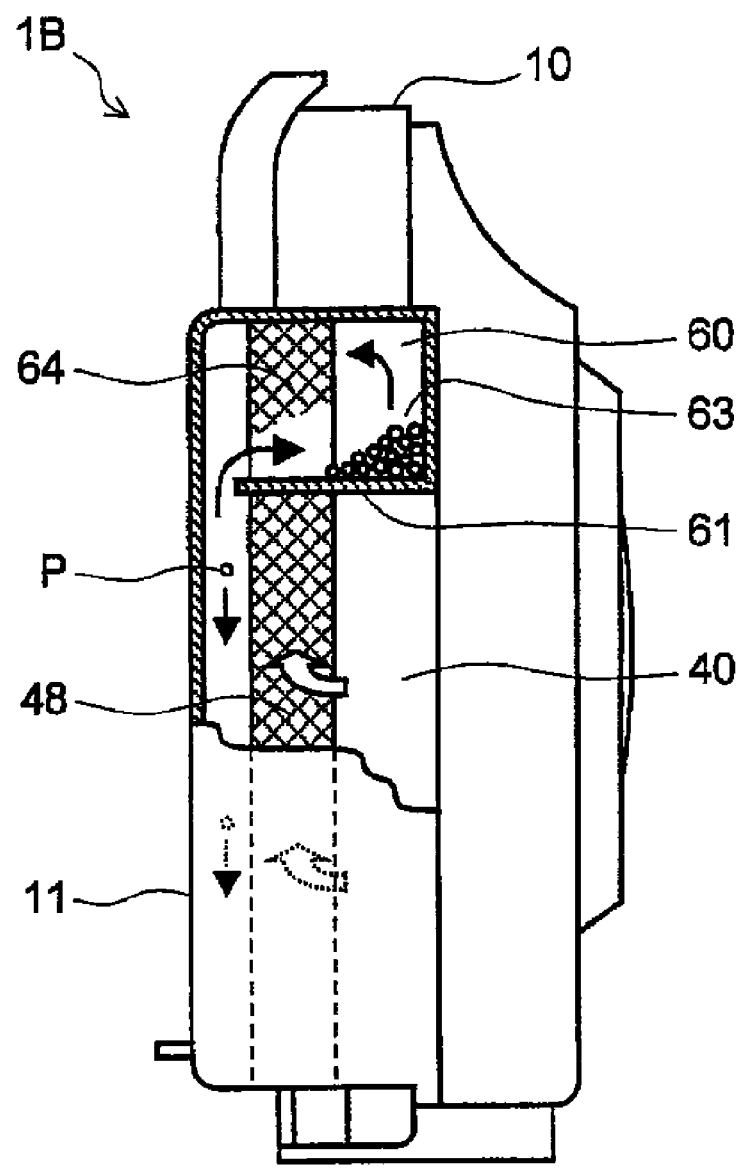
FIG. 6 is a partial cutaway side view of the air purifier of the second embodiment.
Figure 7:
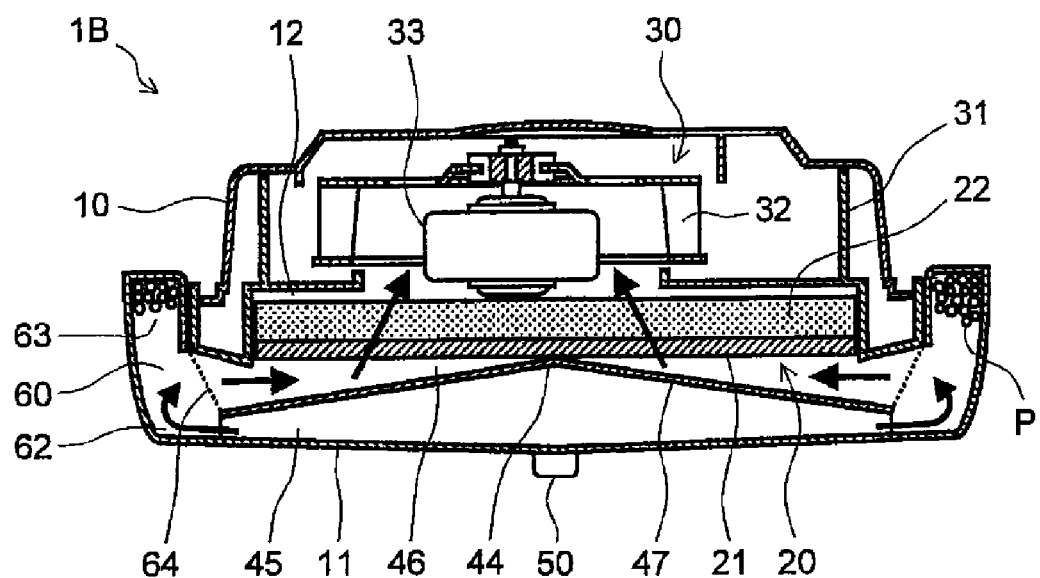
FIG. 7 is a sectional view taken on the line B-B of FIG. 5.

Next, a second embodiment of the invention will be described with reference to FIGS. 5 to 7. FIG. 5 is a partial cutaway front view of an air purifier, FIG. 6 is a partial cutaway side view thereof, and FIG. 7 is a sectional view taken on the line B-B of FIG. 5. It is to be noted that such components as find their functionally equivalent counterparts in the first embodiment are identified with the same reference numerals, and description thereof will be omitted. The same is the case with third and fourth embodiments.

In the first embodiment, the air purifier 1A is provided with the air vents 47 formed in the upper portion of the partition plate 44; in the second embodiment, an air purifier 1B is not provided with them. Instead, at the right and left ends of the upper portion of the partition plate 44, there are provided diverting guide paths 60 for diverting the air that has entered the front panel rear space 45 into the filter unit front space 46. The diverting guide paths 60 are each formed by separating the upper portion of the guide path 40 with a horizontal partition plate 61.

The diverting guide paths 60 each have a second sharp turn corner 62 where the front panel 11 and the air guide plate 41 are joined together, and a pocket-shaped second coarse dust collector 63 for collecting the coarse dust separated from the airflow at the second sharp turn corner 62. Netted filters 64 are provided at the entries of the filter unit front space 46 facing the diverting guide paths 60.

The air purifier 1B operates as follows. When the air blower 30 is driven, the indoor air is sucked in through the air intakes 42. Part of the airflow sucked in through the air intakes 42 passes through the filters 48 and enters the filter unit front space 46. Any coarse dust P trying to enter the filter unit front space 46 is blocked by the filter 48. The other part of the airflow, which has not entered the filter unit front space 46, takes a sharp turn at the sharp turn corners 43 together with the coarse dust P, and then enters the front panel rear space 45.

After the coarse dust P is separated from the airflow that has entered the front panel rear space 45, the airflow passes through the diverting guide paths 60 and enters the filter unit front space 46. When the airflow enters the filter unit front space 46 through the diverting guide paths 60, it takes a sharp turn at the second sharp turn corners 62. As a result, even if coarse dust P is still carried by the airflow at this point, it is separated from the airflow while moving straight forward inertially, and is then collected by the second coarse dust collectors 63. The coarse dust remaining in the airflow that has made a sharp turn is captured by the netted filters 64.

As described above, the air purifier 1B captures the coarse dust P once again with the second sharp turn corners 62 and the second coarse dust collectors 63 when the air is guided from the front panel rear space 45 to the filter unit front space 46. This makes it possible to feed the air containing a smaller amount of coarse dust to the filter unit 20, thereby preventing clogging of the filter unit 20.

As a result of the netted filters 64 being provided in the air passage between the front panel rear space 45 and the filter unit front space 46, even if coarse dust P is still carried by the air moving from the front panel rear space 45 to the filter unit front space 46, it is captured by the netted filters 64 before reaching the filter unit 20.

The idea of providing a netted filter in the air passage between the front panel rear space 45 and the filter unit front space 46 can be applied to the air purifier 1A of the first embodiment. In this case, the netted filter is provided over the air vents 47.

Figure 8:
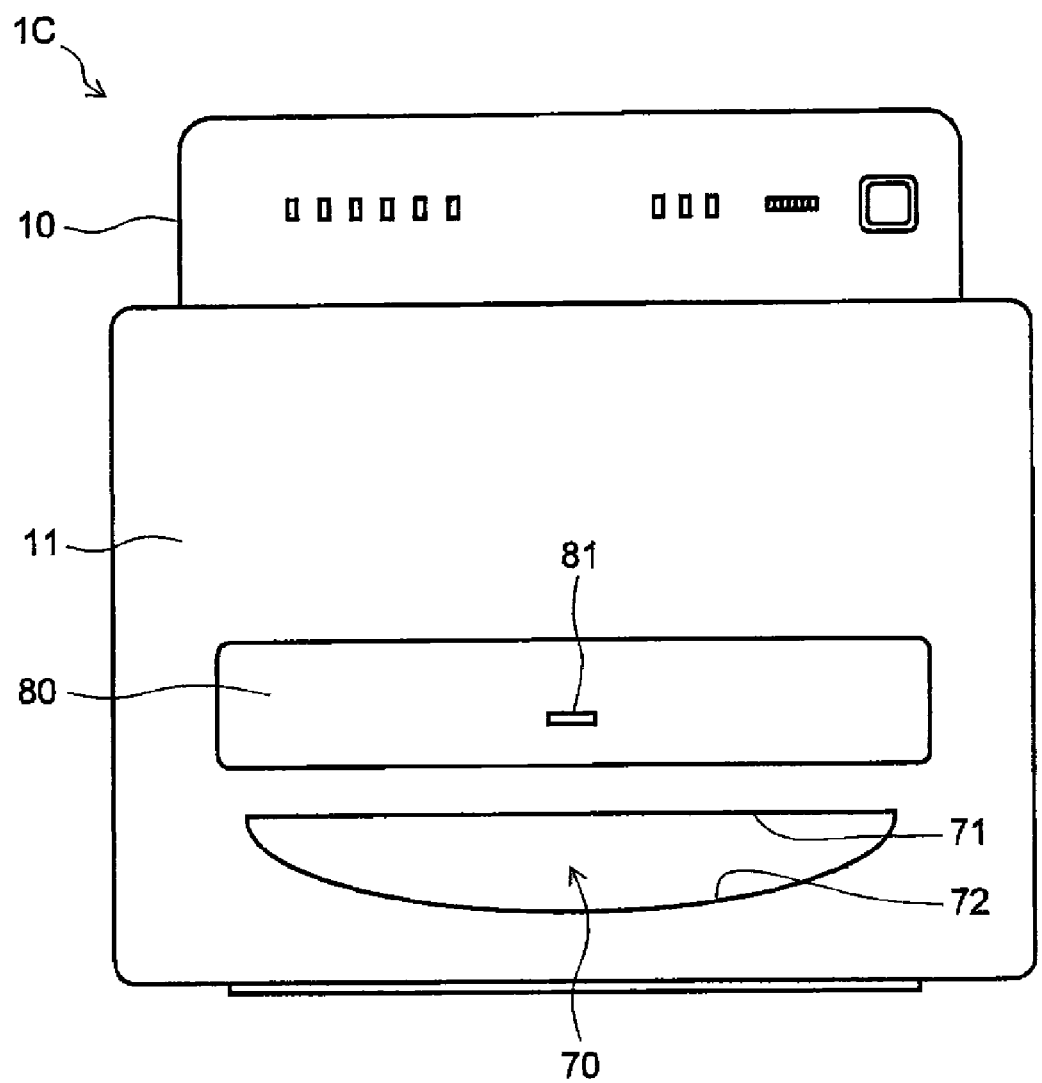
FIG. 8 is a front view of an air purifier according to a third embodiment of the invention.
Figure 9:
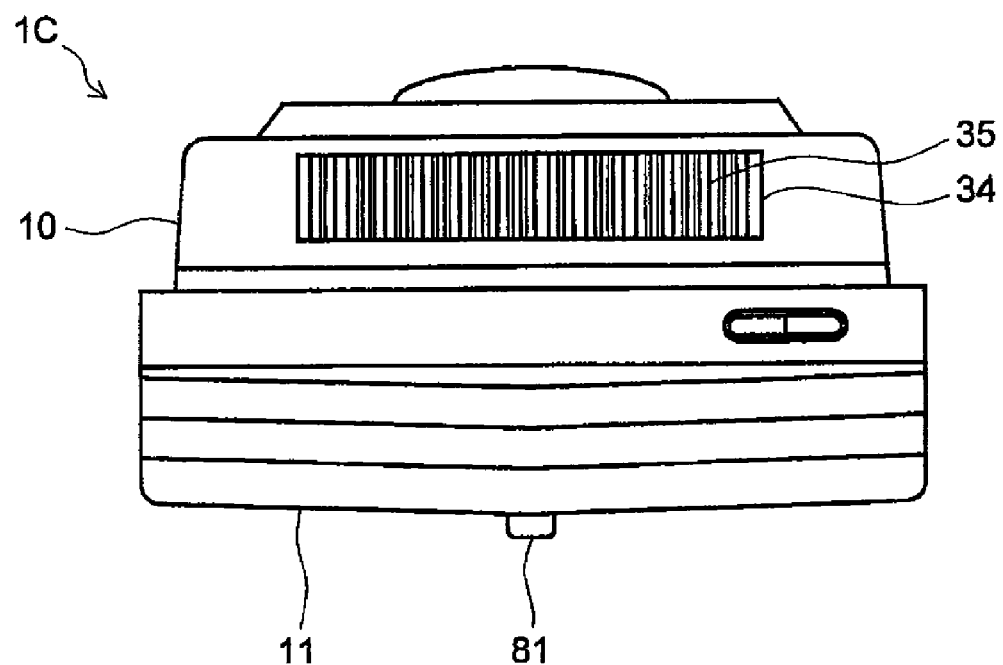
FIG. 9 is a top view of the air purifier of the third embodiment.
Figure 10:
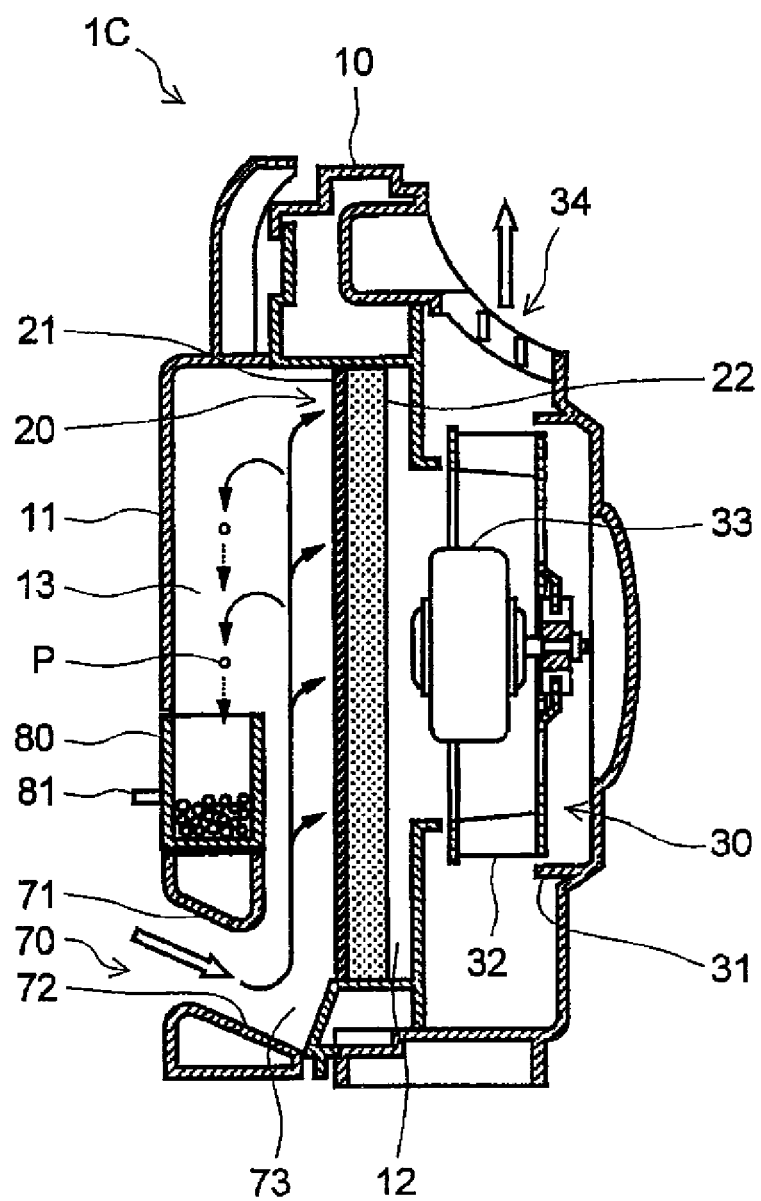
FIG. 10 is a vertical sectional view of the air purifier of the third embodiment.

Next, a third embodiment of the invention will be described with reference to FIGS. 8 to 10. FIG. 8 is a front view of an air purifier, FIG. 9 is a top view of the air purifier, and FIG. 10 is a vertical sectional view of the air purifier.

In an air purifier 1C according to the third embodiment, a space between the front panel 11 and the filter unit 20 serves as an airflow passage 13 for delivering an airflow to the filter unit 20. In the lower portion of the front panel 11 is formed a guide path 70 for guiding the indoor air to the airflow passage 13. The guide path 70 is built with an upper air guide plate 71 and a lower air guide plate 72. The air guide plates 71 and 72 are sloped so that the indoor air is guided obliquely downward.

As shown in FIG. 8, the lower air guide plate 72 is curved downward, as seen in a front view. This makes the guide path 70 look like a first quarter moon, as seen in a front view, with the width being broader at the middle thereof than at both ends thereof.

At the back of the guide path 70 is formed a sharp turn corner 73 for making the airflow take a sharp upward turn. The cross-sectional area of the airflow passage 13 leading out of the sharp turn corner 73 on the most upstream side of the filter unit 20 is approximately the same as that of the guide path 70.

The front panel 11 is fitted with a dust box 80 in a position located above the guide path 70. The dust box 80, which slides into the airflow passage 13 like a drawer, is open in the upper face and has a knob 81 in the front face. The airflow that has made a sharp turn at the sharp turn corner 73 moves upward, passing through the space between the dust box 80 and the filter unit 20. The width of the space between the dust box 80 and the filter unit 20 is narrower than that of the airflow passage 13 located above the space, resulting in the formation of a bottleneck.

The air purifier 1C operates as follows. When the air blower 30 is driven, a negative pressure is produced behind the filter unit 20. This results in the formation of the airflow that is sucked in through the guide path 70, passes through the filter unit 20, and is then blown out of the air outlet 34. The airflow sucked in through the guide path 70 is guided obliquely downward, takes a sharp turn at the sharp turn corner 73, and then moves upward into the airflow passage 13.

The airflow that has entered the airflow passage 13 is gradually sucked into the filter unit 20 while moving linearly upward along the filter unit 20. The airflow takes a right-angled turn when it is sucked into the filter unit 20. On the other hand, the coarse dust P in the airflow keeps moving straight upward inertially. Upon reaching the upper portion of the airflow passage 13, the coarse dust P is separated, by the swirling flow formed in the airflow passage 13 located above the bottleneck, from the airflow that is being sucked into the filter unit 20, and then falls into the dust box 80 by gravity. This makes it possible to collect the coarse dust P in the air in the dust box 80 without making it stick to the filter unit 20.

Since the guide path 70 guides the airflow obliquely downward, the airflow moves obliquely downward, takes a turn at a sharp angle, and then moves upward. This increases the speed at which the airflow moves and hence the inertial force of the coarse dust P. As a result, coarse dust separation capability is improved.

Moreover, since the lower air guide plate 72 is curved downward, as seen in a front view, the pressures between an area of the guide path 70 closer to the air blower 30 and an area thereof farther away from the air blower 30 are equalized. This makes the airflow move straight, as seen in a front view, resulting in an increase in the speed at which the airflow moves. As a result, coarse dust separation capability is improved.

Furthermore, since the cross-sectional area of the guide path 70 is approximately the same as that of the airflow passage 13 on the most upstream side of the filter unit 20, the airflow from the guide path 70 passes straight through the airflow passage 13 on the most upstream side of the filter unit 20, resulting in an increase in the speed at which the airflow moves. As a result, coarse dust separation capability is improved.

The airflow from which the coarse dust P is separated passes through the filter unit 20, and is then sucked in by the air blower 30. In that process, odors in the air are removed by the odor removal filter 21, and fine dust is captured by the dust collecting filter 22. The air that has purified by the filter unit 20 is blown out of the air outlet 34. In this way, the circulation of the airflow is produced in a room such that the air is sucked in obliquely downward through the guide path 70 and is then blown out of the air outlet 34 in the upward direction.

Figure 11:
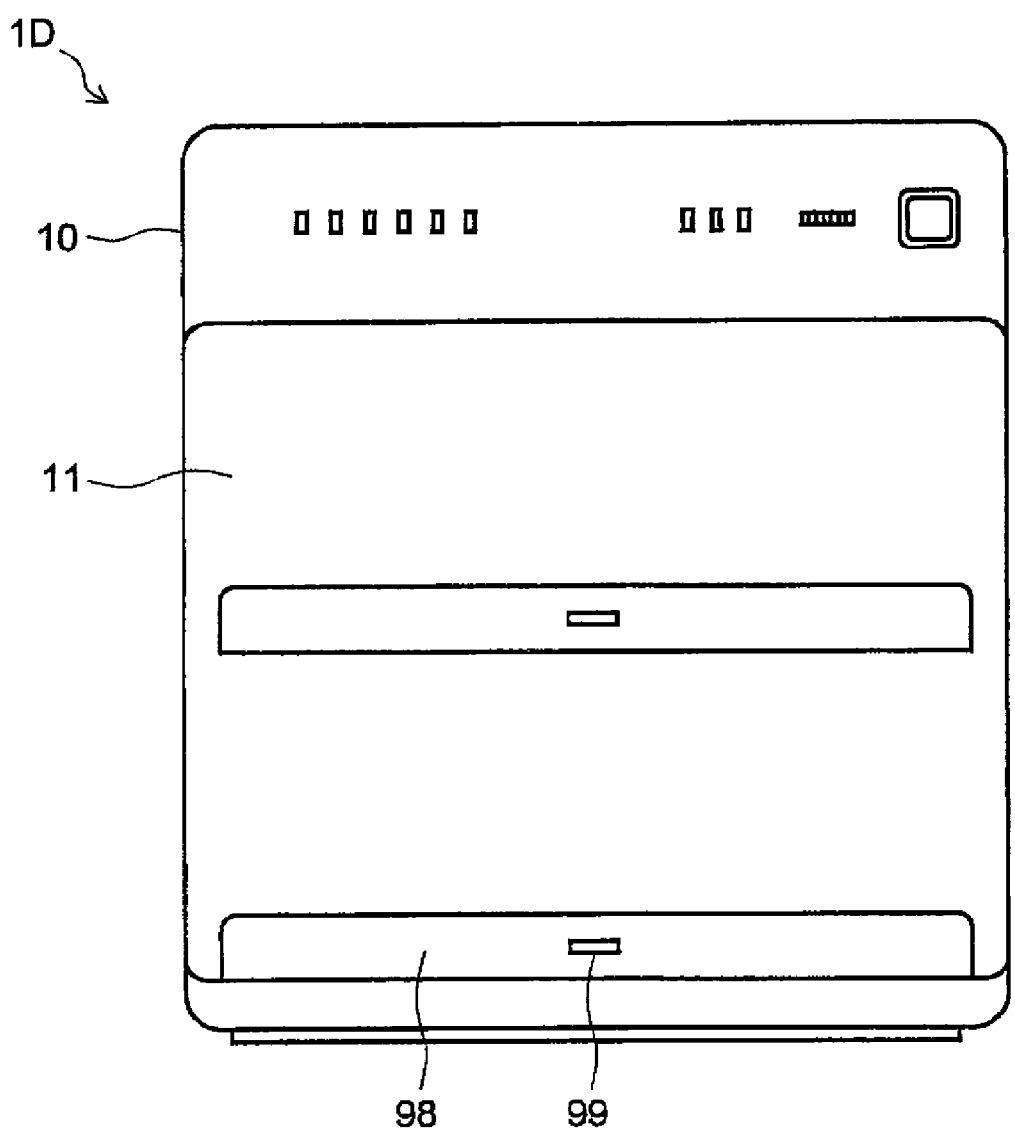
FIG. 11 is a front view of an air purifier according to a fourth embodiment of the invention.
Figure 12:
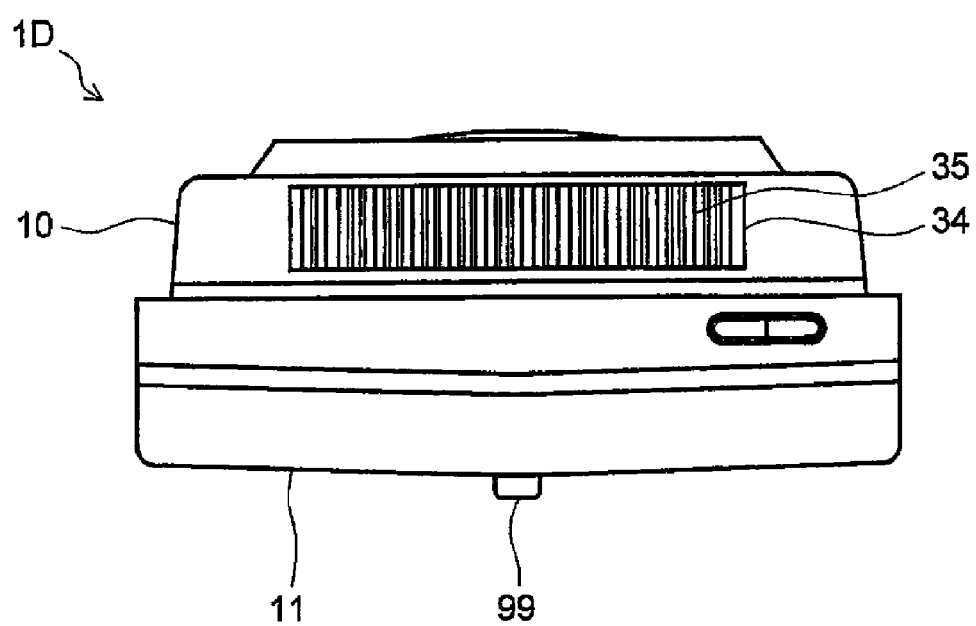
FIG. 12 is a top view of the air purifier of the fourth embodiment.
Figure 13:
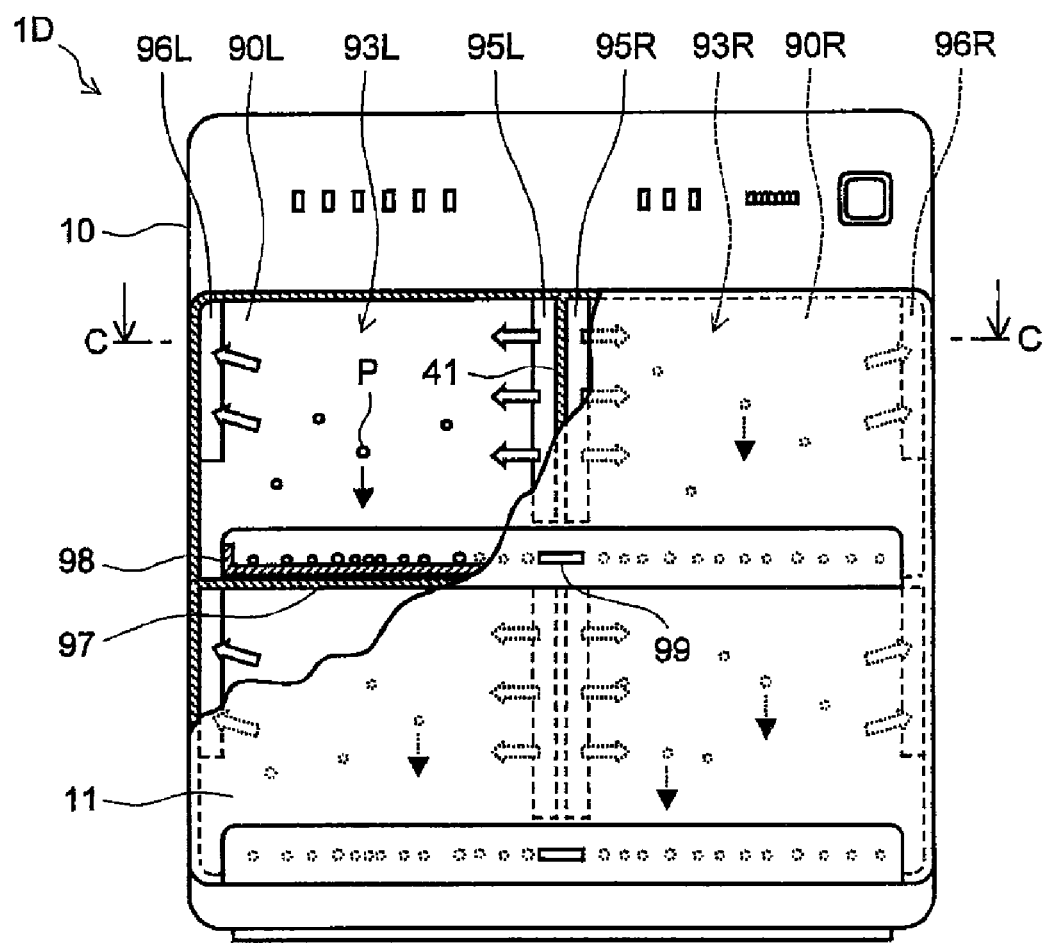
FIG. 13 is a partial sectional front view of the air purifier of the fourth embodiment.
Figure 14:
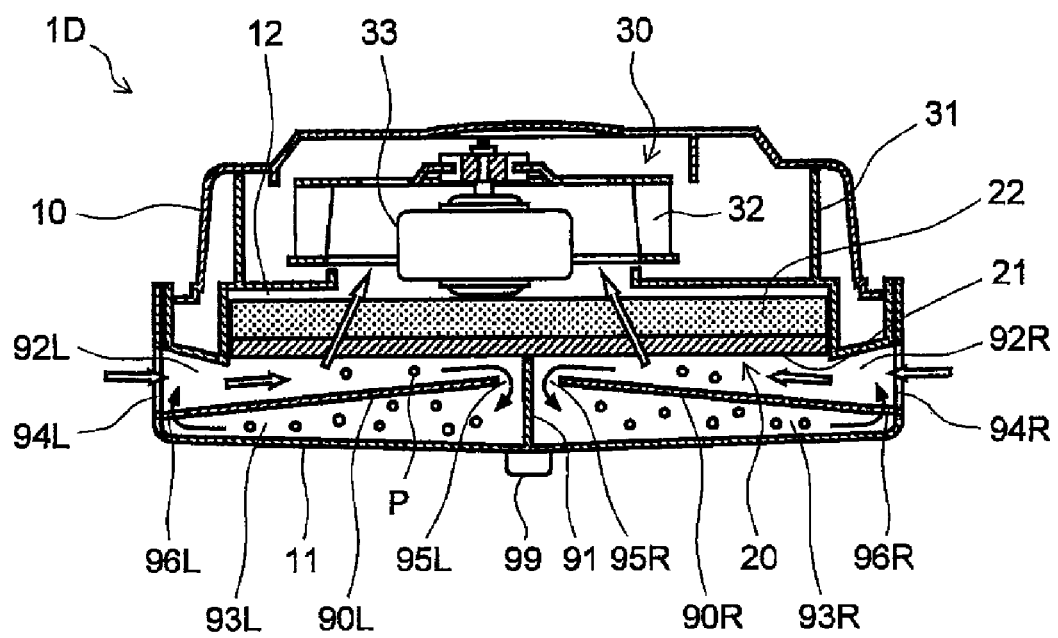
FIG. 14 is a sectional view taken on the line C-C of FIG. 13.

Next, a fourth embodiment of the invention will be described with reference to FIGS. 11 to 14. FIG. 11 is a front view of an air purifier, FIG. 12 is a top view of the air purifier, FIG. 13 is a partial sectional front view of the air purifier, and FIG. 14 is a sectional view taken on the line C-C of FIG. 13.

In an air purifier 1D according to the fourth embodiment, in a space between the front panel 11 and the filter unit 20 are disposed air guide plates 90L and 90R in such a way that the space is divided into front and rear spaces. The space between the filter unit 20 and the air guide plates 90L and 90R serves as a guide path, and the space between the front panel 11 and the air guide plates 90L and 90R serves as a coarse dust collector. As shown in FIG. 14, in the fourth embodiment, the air guide plates 90L and 90R are a matched pair of plates and are symmetric. That is, the air guide plates 90L and 90R are disposed on the left and right sides, respectively, so as to be symmetric. Between the air guide plates 90L and 90R, a vertical divider plate 91 protrudes from the back face of the front panel 11. The divider plate 91 makes contact with the filter unit 20 at the edge thereof, whereby the space between the front panel 11 and the filter unit 20 is divided into right and left spaces.

The air guide plate 90L marks the boundary between a guide path 92L and a coarse dust collector 93L, and the air guide plate 90R marks the boundary between a guide path 92R an a coarse dust collector 93R. The air guide plates 90L and 90R are disposed diagonally to the filter unit 20 in a horizontal plane. That is, as for the air guide plate 90L, the left end of the guide path 92L is a larger-width end and the right end thereof is a smaller-width end; as for the air guide plate 90R, the right end of the guide path 92R is a larger-width end and the left end thereof is a smaller-width end.

Both of the guide paths 92L and 92R lead to the outside at their respective larger-width ends, where air intakes 94L and 94R that communicate with the outside are formed. The guide paths 92L and 92R arrive, at their respective smaller-width ends, at the middle of the filter unit 20, where the air guide plates 90L and 90R have formed therein vertically long slits that communicate with the coarse dust collectors 93L and 93R. These slits serve as sharp turn corners 95L and 95R.

The air guide plates 90L and 90R have formed therein air vents 96L and 96R for circulating the air that has flowed into the coarse dust collectors 93L and 93R back into the guide paths 92L and 92R. The air vents 96L and 96R are formed in the upper portions of the coarse dust collectors 93L and 93R on those sides which are closer to the air intakes 94L and 94R.

At the lower portion of the coarse dust collectors 93L and 93R, a detachable dust box 98 is provided. In this fourth embodiment, the coarse dust collectors 93L and 93R each have a two-tiered structure. That is, under the coarse dust collectors 93L and 93R are provided another coarse dust collectors 93L and 93R. The upper coarse dust collectors 93L and 93R and the lower coarse dust collectors 93L and 93R are separated by a horizontal partition 97 (see FIG. 13) formed on the back of the front panel 11. Since the coarse dust collectors 93L and 93R each have a two-tiered structure, the guide paths 92L and 92R, the air intakes 94L and 94R, the sharp turn corners 95L and 95R, and the air vents 96L and 96R also each have a two-tiered structure.

The dust box 98 is provided in such a way that both the coarse dust collectors 93L and 93R are covered by a single dust box 98. It is needless to say that the dust box 98 also has a two-tiered structure. The dust box 98, which slides into the coarse dust collectors 93L and 93R, like a drawer, from the front of the front panel 11, is open in the upper face and has a knob 99 in the front face.

The air purifier 1D operates as follows. When the air blower 30 is driven, a negative pressure is produced behind the filter unit 20. This results in the formation of the airflow that is sucked in through the air intakes 94L and 94R, passes through the filter unit 20, and is then blown out of the air outlet 34. The airflow that has entered the guide paths 92L and 92R through the air intakes 94L and 94R is gradually sucked into the filter unit 20 while horizontally moving linearly along the filter unit 20. The airflow takes a right-angled turn when it is sucked into the filter unit 20. On the other hand, the coarse dust P in the airflow keeps moving straight inertially. Upon reaching the innermost portions of the guide paths 92L and 92R, the airflow turns the sharp turn corners 95L and 95R into the coarse dust collectors 93L and 93R. This sharp turn of the airflow causes the coarse dust P to be separated from the airflow. The separated coarse dust P falls into the dust box 98 by gravity. This makes it possible to collect the coarse dust P in the airflow in the dust box 98 without making it stick to the filter unit 20.

The air that has flowed into the coarse dust collectors 93L and 93R returns to the guide paths 92L and 92R through the air vents 96L and 96R. This allows the air to flow smoothly from the guide paths 92L and 92R to the coarse dust collectors 93L and 93R, making it possible to efficiently introduce the coarse dust P into the coarse dust collectors 93L and 93R. Since the air vents 96L and 96R are formed in the upper portions of the coarse dust collectors 93L and 93R, the airflow is made to pass through an area away from the coarse dust P collected in the bottom of the dust box 98. This prevents the collected coarse dust P from being stirred up and drawn back into the airflow. In addition, since the air vents 96L and 96R are disposed near the air intakes 94L and 94R, the air inside the coarse dust collectors 93L and 93R is sucked in therethrough to the entries of the guide paths 92L and 92R. As a result, even when the air that has been sucked in still contains dust, the dust is captured by the filter unit 20, or is separated from the airflow when the airflow takes another turn at the sharp turn corners 95L and 95R. This helps realize a thorough removal of dust.

In the fourth embodiment, there are provided two of the air guide plates 90L and 90R so as to be symmetric, and the divider plate 91 protrudes between them to form the sharp turn corners 95L and 95R on the left and right sides thereof. With this structure, irrespective of whether the airflow is sucked in from the right or left side, the airflow is guided from the ends of the filter unit 20 to the middle thereof, that is, from a region where the suction power of the air blower 30 is relatively weak to a region where the suction power is relatively strong. This results in the formation of a stable airflow that can reach the innermost portions of the guide paths 92L and 92R without fail.

Additionally, in the fourth embodiment, the coarse dust collectors 93L and 93R each have a two-tiered structure. This decreases the distance over which the coarse dust P in each coarse dust collector falls, allowing it to fall in the dust box 98 without delay. This makes it possible to reduce the percentage of coarse dust P that will be carried away by the airflow before it falls to the bottom.

The airflow from which the coarse dust P is separated passes through the filter unit 20, and is then sucked in by the air blower 30. In that process, odors in the air are removed by the odor removal filter 21, and fine dust is captured by the dust collecting filter 22. The air that has purified by the filter unit 20 is blown out of the air outlet 34.

As the air purifier 1D is continuously operated, the coarse dust P is gradually collected in the dust box 98. When the amount of collected coarse dust becomes large, the air purifier 1 is stopped, and the dust box 98 is taken out for the disposal of the coarse dust P collected therein. The emptied dust box 98 is reinstalled in the air purifier 1D, and the operation is resumed. Preferably, at least part of the dust box 98 is made of transparent material, so that the amount of coarse dust collected therein can be seen though at a glance.

Since the dust box 98 singly covers both the coarse dust collectors 93L and 93R, the number of dust boxes 98 is smaller than that of coarse dust collectors. This reduces the trouble of disposing of the coarse dust.

It is to be understood that the present invention may be practiced in any other manner than specifically described above as embodiments, and various modifications are possible within the scope of the invention.

INDUSTRIAL APPLICABILITY

The present invention finds wide application in air purifiers that purify indoor air, air conditioners, electric ceramic fan heaters, kerosene fan heaters, and the like.

The invention claimed is:

1. An air purifier, comprising:
   an air blower circulating indoor air;
   a filter unit placed in a circulating airflow of the indoor air, the filter unit capturing dust in the air; and
   a guide path guiding the indoor air to the filter unit,
   wherein the guide path is followed by:
      a sharp turn corner for the airflow;
      a fixed partition plate provided downstream of the sharp turn corner; and
      a coarse dust collector collecting coarse dust separated from the airflow that has made a sharp turn and reduced in speed,
   wherein the fixed partition plate separates a first space defined by a first side of the fixed partition plate and the filter unit, from a second space defined by a second side, opposite to the first side, of the fixed partition plate and the coarse dust collector, the second space gradually increases in area of the airflow to reduce a speed of the airflow, and
   wherein part of the airflow that has made the sharp turn is separated and fed, together with the coarse dust, into the second space such that the coarse dust is collected in the coarse dust collector.

2. An air purifier, comprising:
   an air blower circulating indoor air;
   a filter unit placed in a circulating airflow of the indoor air, the filter unit capturing dust in the air; and
   a guide path guiding the indoor air to the filter unit,
   wherein the guide path is followed by:
      a sharp turn corner for the airflow; and
      a first coarse dust collector collecting coarse dust separated from the airflow that has made a sharp turn,
   wherein the guide path is formed behind a front panel placed in front of the filter unit,
   wherein the front panel has rear-facing air intakes formed on right and left sides thereof, and the sharp turn corner just past an entry of each air intake, and
   wherein in a lower portion of the front panel is provided a detachable dust box serving as the coarse dust collector.

3. The air purifier of claim 2,
   wherein a space between the front panel and the filter unit is partitioned by a vertical partition plate into a front panel rear space and a filter unit front space, wherein the partition plate faces, at right and left ends thereof, the sharp turn corners, and a space between the front panel and the partition plate becomes narrower at right and left ends thereof and becomes broader in a middle thereof, wherein in an upper portion of the partition plate are formed a plurality of air vents arranged in a horizontal row, so that the front panel rear space is communicated with the filter unit front space.

4. The air purifier of claim 2,
wherein a space between the front panel and the filter unit is partitioned by a vertical partition plate into a front panel rear space and a filter unit front space, wherein the partition plate faces, at right and left ends thereof, the sharp turn corners, and a space between the front panel and the partition plate becomes narrower at right and left ends thereof and becomes broader in a middle thereof, wherein at the right and left ends of the partition plate are provided diverting guide paths diverting the air that has entered the front panel rear space into the filter unit front space, wherein the diverting guide paths each have a second sharp turn corner and a second coarse dust collector.

5. The air purifier of claim 3, wherein
a netted filter is provided at an entry of the filter unit front space facing the guide path.

6. The air purifier of claim 3, wherein
a netted filter is provided in an air passage between the front panel rear space and the filter unit front space.

7. An air purifier, comprising:
an air blower circulating indoor air;
a filter unit placed in a circulating airflow of the indoor air, the filter unit capturing dust in the air; and
a guide path guiding the indoor air to the filter unit,
wherein the guide path is followed by:
   a sharp turn corner for the airflow; and
   a coarse dust collector collecting coarse dust separated from the airflow that has made a sharp turn,
wherein the guide path is formed in a lower portion of a front panel placed in front of the filter unit,
wherein at a back of the guide path is formed the sharp turn corner that makes the airflow take a sharp upward turn and thereby guides the airflow to a front of the filter unit, and
wherein the front panel is fitted with a dust box in a position located above the guide path, the dust box collecting the coarse dust separated from the airflow sucked into the filter unit.

8. The air purifier of claim 7, wherein
the guide path is built with upper and lower air guide plates that guide the indoor air obliquely downward.

9. The air purifier of claim 8, wherein
the lower air guide plate is curved downward, as seen in a front view.

10. The air purifier of claim 7, wherein
a cross-sectional area of the guide path is approximately a same as a cross-sectional area of an airflow passage on a most upstream side of the filter unit.

11. An air purifier, comprising:
an air blower circulating indoor air;
a filter unit placed in a circulating airflow of the indoor air, the filter unit capturing dust in the air; and
a guide path guiding the indoor air to the filter unit,
wherein the guide path is followed by:
   a sharp turn corner for the airflow; and
   a coarse dust collector collecting coarse dust separated from the airflow that has made a sharp turn,
wherein, in a space between the filter unit and a front panel placed in front of the filter unit, an air guide plate is disposed diagonally to the filter unit in a horizontal plane, such that the guide path is formed between the air guide plate and the filter unit,
wherein the guide path has a larger-width end at one end of the air guide plate, and has a smaller-width end at another end thereof, and
wherein the guide path is provided, at the larger-width end thereof, with an air intake leading to an outside, and provided, at the smaller-width end thereof, with the sharp turn corner communicating with the coarse dust collector located between the air guide plate and the front panel.

12. The air purifier of claim 11, wherein
the air guide plate has formed therein an air vent for circulating the air that has flowed into the coarse dust collector back into the guide path.

13. The air purifier of claim 12, wherein
the air vent is formed in an upper portion of the coarse dust collector.

14. The air purifier of claim 12, wherein
the air vent is disposed near the air intake.

15. The air purifier of claim 11, wherein
in a lower portion of the coarse dust collector, a detachable dust box is provided.

16. The air purifier of claim 11,
wherein two of the air guide plates are provided so as to be symmetric,
wherein a divider plate is provided between the air guide plates to form the sharp turn corners on right and left sides thereof.

17. The air purifier of claim 16, wherein
a dust box singly covers both right and left sections of the coarse dust collector.

18. The air purifier of claim 11, wherein
the coarse dust collector has a multiple-tiered structure.

19. The air purifier of claim 4, wherein
a netted filter is provided at an entry of the filter unit front space facing the guide path.

20. The air purifier of claim 4, wherein
a netted filter is provided in an air passage between the front panel rear space and the filter unit front space.

* * * * *